（12) United States Patent
Aqad et al.

(10) Patent No.: US 11,550,217 B2
(45) Date of Patent: *Jan. 10, 2023

(54) PHOTORESIST COMPOSITION, COATED SUBSTRATE INCLUDING THE PHOTORESIST COMPOSITION, AND METHOD OF FORMING ELECTRONIC DEVICE

(71) Applicant: ROHM AND HAAS ELECTRONIC MATERIALS LLC, Marlborough, MA (US)

(72) Inventors: Emad Aqad, Northborough, MA (US); William Williams, III, Ipswich, MA (US); James F. Cameron, Brookline, MA (US)

(73) Assignee: ROHM AND HAAS ELECTRONIC MATERIALS LLC, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/387,788

(22) Filed: Dec. 22, 2016

(65) Prior Publication Data
US 2017/0192353 A1    Jul. 6, 2017

Related U.S. Application Data

(60) Provisional application No. 62/273,523, filed on Dec. 31, 2015.

(51) Int. Cl.
| G03F 7/04 | (2006.01) |
|---|---|
| G03F 7/09 | (2006.01) |
| G03F 7/38 | (2006.01) |
| G03F 7/40 | (2006.01) |
| C07C 321/28 | (2006.01) |
| C07C 25/18 | (2006.01) |
| G03F 7/004 | (2006.01) |
| G03F 7/039 | (2006.01) |
| C07C 255/24 | (2006.01) |
| C07C 381/12 | (2006.01) |
| C07C 255/31 | (2006.01) |
| C07C 255/34 | (2006.01) |
| G03F 7/038 | (2006.01) |
| G03F 7/16 | (2006.01) |
| G03F 7/20 | (2006.01) |
| G03F 7/32 | (2006.01) |
| C07C 303/32 | (2006.01) |

(52) U.S. Cl.
CPC ............ *G03F 7/0045* (2013.01); *C07C 25/18* (2013.01); *C07C 255/24* (2013.01); *C07C 255/31* (2013.01); *C07C 255/34* (2013.01); *C07C 321/28* (2013.01); *C07C 381/12* (2013.01); *G03F 7/038* (2013.01); *G03F 7/039* (2013.01); *G03F 7/0397* (2013.01); *G03F 7/091* (2013.01); *G03F 7/162* (2013.01); *G03F 7/168* (2013.01); *G03F 7/2006* (2013.01); *G03F 7/322* (2013.01); *G03F 7/38* (2013.01); *G03F 7/40* (2013.01); *C07C 2602/08* (2017.05); *C07C 2603/74* (2017.05)

(58) Field of Classification Search
CPC ... G03F 7/0045; G03F 7/0397; C07C 303/32; C07C 321/28; C07C 25/18
USPC ...... 430/270.1, 326, 921; 526/100, 108, 109, 526/113; 568/18
See application file for complete search history.

(56) References Cited

U.S. PATENT DOCUMENTS

| 2,766,243 A | 10/1956 | Middleton |
|---|---|---|
| 5,273,840 A | 12/1993 | Dominey |
| 5,554,664 A | 9/1996 | Lamanna et al. |
| 5,874,616 A | 2/1999 | Howells et al. |
| 7,304,175 B2 | 12/2007 | Harada et al. |
| 7,655,379 B2 | 2/2010 | Glodde et al. |
| 8,124,803 B2 | 2/2012 | Yoshida et al. |
| 8,241,831 B2* | 8/2012 | Jung ............... C07C 309/68 430/270.1 |
| 8,338,076 B2 | 12/2012 | Kawaue et al. |
| 8,932,797 B2* | 1/2015 | Thackeray ........ G03F 7/0045 430/270.1 |
| 2002/0009635 A1 | 1/2002 | Michot et al. |

(Continued)

FOREIGN PATENT DOCUMENTS

| JP | 2006251466 A | 9/2006 |
|---|---|---|
| JP | 2011046696 A | 3/2011 |

(Continued)

OTHER PUBLICATIONS

Glodde et al.; "Fluorine-free Photoacid Generators for 193 nm Lithography Based on Non-Sulfonate Organic Superacids"; Journal of Photopolymer Science and Technology; vol. 23; No. 2; 2010; pp. 173-184.

(Continued)

*Primary Examiner* — John S Chu
(74) *Attorney, Agent, or Firm* — Cantor Colburn LLP

(57) ABSTRACT

A photoresist composition, including an acid-sensitive polymer and photoacid generator compound having Formula (I):

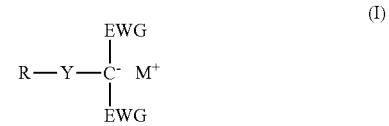

wherein, EWG, Y, R, and M+ are the same as described in the specification.

21 Claims, No Drawings

(56) References Cited

U.S. PATENT DOCUMENTS

| | | |
|---|---|---|
| 2003/0066988 A1 | 4/2003 | Michot et al. |
| 2006/0194982 A1 | 8/2006 | Harada et al. |
| 2006/0204890 A1 | 9/2006 | Kodama |
| 2007/0027336 A1 | 2/2007 | Yoshida et al. |
| 2007/0111138 A1 | 5/2007 | Rahman et al. |
| 2009/0176175 A1 | 7/2009 | Glodde |
| 2009/0181319 A1 | 7/2009 | Li et al. |
| 2009/0181320 A1 | 7/2009 | Li et al. |
| 2010/0304289 A1 | 12/2010 | Mimura et al. |
| 2010/0323294 A1 | 12/2010 | Li et al. |
| 2011/0001190 A1* | 1/2011 | Ide ............... C08G 77/388 257/347 |
| 2011/0008731 A1 | 1/2011 | Yamaguchi et al. |
| 2011/0065857 A1 | 3/2011 | Terui et al. |
| 2011/0223535 A1 | 9/2011 | Liu et al. |
| 2011/0250542 A1 | 10/2011 | Liu et al. |
| 2011/0269074 A1 | 11/2011 | Aqad et al. |
| 2011/0287361 A1 | 11/2011 | Bae et al. |
| 2011/0300484 A1 | 12/2011 | Yamato et al. |
| 2012/0156618 A1 | 6/2012 | Takahashi et al. |
| 2012/0203024 A1 | 8/2012 | Oh et al. |
| 2013/0034706 A1 | 2/2013 | Yamaguchi |
| 2013/0137037 A1 | 5/2013 | Yamanaka et al. |
| 2015/0064620 A1 | 3/2015 | Kaur et al. |
| 2015/0338736 A1 | 11/2015 | Kawabata et al. |
| 2017/0192352 A1* | 7/2017 | Williams, III ........ G03F 7/0045 |
| 2019/0256683 A1* | 8/2019 | Dhaliwal ................ C08L 23/02 |

FOREIGN PATENT DOCUMENTS

| | | | |
|---|---|---|---|
| JP | 2011048111 A | 3/2011 | |
| JP | 2011053364 A | 3/2011 | |
| JP | 2012032671 A | 2/2012 | |
| JP | 2014-156585 A | 8/2014 | |
| JP | 2015114632 A | 6/2015 | |
| WO | 2004002955 A2 | 1/2004 | |
| WO | 2009087027 A2 | 7/2009 | |
| WO | 2011-016425 A1 | 2/2011 | |

OTHER PUBLICATIONS

Kutt et al.; "Equilibrium Acidities of Superacids"; J. Org. Chem.; 2011; vol. 76; No. 2; pp. 391-395.

Little et al.; "Cyancoarbon Chemistry. X. Pyridines from Tetracyanopropenes"; Journal of American Chemical Society; vol. 80; 1958; pp. 2832-2838.

Middleton et al.; "Cyanocarbon Chemistry. V. Cyancarbon Acids and their Salts"; Journal of the American Chemical Society; vol. 80; 1958; pp. 2795-2806.

Morales et al.; "Design, Synthesis, and Structural and Spectroscopis Studies of Push-Pull Two-Photon Absorbing Chromophores with acceptor Groups of Varying Strength"; Journal of Organic Chemistry; vol. 78; No. 3; 2013; pp. 1014-1025.

Padmanaban et al.; "Performance of Imida and Methide Onium PAGs in 193nm Resist Formulations"; SPIE; vol. 5039; 2003; pp. 743-751.

Piper et al.; "Syntheses and Antifolate Activity of 5-Methyl-5-deaza Analogues of Aminopterin, Methotrexate, Folic Acid, and N10-Methylfolic Acid"; Journal of Medicinal Chemistry; vol. 29; 1986; pp. 1080-1087.

Schmidt et al.; "The synthesis of alkoxymethylene malononitriles, tetracyanopropenides and highly substituted a-aminopyridines"; Monatshefte Fur Chemie 108; (1977); pp. 895-900.

Crivello J. V. "The Discovery and Development of Onium Salt Cationic Photoinitiators", Journal of Polymer Science: Part A: Polymer Chemistry, vol. 37, pp. 4241-4254 (1999).

Telitel et al. "The 1,3-bis(dicyanomethylidene)indane skeleton as a (photo) initiator in thermal ring opening polymerization at RT and radical or cationic photopolymerization" RSC Adv. 2014, vol. 4, 15930-15936.

Han "Studies on Synthesis of Sulfonium Salts and Their Properties as Photo-acid Generator", Chinese Master's Theses Full-text database, Engineering Science and Technology I, No. 2 (2007) (6 pages).

Wang et al. "Studies on Synthesis of Sulfonium Salts and Their Properties as Photo-acid Generator" Imaging Science and Photochemistry, vol. 26, No. 2 (2008), pp. 88-93 (with English abstract).

Shirai et al. "Photoacid and Photobase Generators: Chemistry and Applications to Polymeric Materials" Prog. Polym. Sco., vol. 21, pp. 1-45, (1996).

Tamamura et al. "Organic Charge Transfer Salts. II. Emission Spectrum of an Organic Charge Transfer Salt, 2,4,6-Triphenylthiopyrylium-1,1,3,3-tetracynopropenide" Bulletin of the Chemical Society of Japan, 1974, vol. 47(2), pp. 442-447.

Yasuba et al. "Organic Charge Transfer Salts; Absorption Spectra of Salts between the Pyrylium or Thiopyrylium Cation and the 1,1,3,3-Tetracyanopropenide or Tricyanomethanide Anion" Bulletin of the Chemical Society of Japan, 1970, vol. 43, pp. 3101-3106.

* cited by examiner

PHOTORESIST COMPOSITION, COATED SUBSTRATE INCLUDING THE PHOTORESIST COMPOSITION, AND METHOD OF FORMING ELECTRONIC DEVICE

CROSS REFERENCE TO RELATED APPLICATION

This application claims priority to provisional U.S. Application No. 62/273,523, filed on Dec. 31, 2015, the content of which is incorporated herein by reference in its entirety.

FIELD

This invention relates to a photoresist composition including a methide-containing photoacid generator (PAG) compound and a method of forming an electronic device.

INTRODUCTION

Known photoresists can provide features having resolution and size sufficient for many existing commercial applications. However for many other applications, the need exists for new photoresists that can provide highly resolved images of sub-micron dimension.

Various attempts have been made to alter the make-up of photoresist compositions to improve performance of functional properties. Among other things, a variety of photoactive compounds have been reported for use in photoresist compositions. See, for example, U.S. Pat. No. 7,304,175 and U.S. Patent Application Publication No. 2007/0027336. In particular, tailored photoacid generators (PAGs) having controlled acid diffusion and improved miscibility with polymers are very important to meet the challenges for resist materials raised by high resolution lithography. For example, certain defects such as T-topping, foot formation and notching may arise in imaged photoresist films if the PAG is not uniformly distributed within the resist film. It is believed that the structure of the PAG anion plays a critical role in the overall performance of a photoresist by affecting the interaction of the photoacid generator with other photoresist components. These interactions, in turn, have remarkable effects on diffusion characteristics of the photogenerated acid. PAG structure and size greatly affect the homogenous distribution of the PAG in the photoresist film.

In the art, ionic photoacid generator compounds (PAGs), which contain a fluorinated alkylsulfonate group have been widely explored. Upon photochemical decomposition, these PAGs produce an exceptionally strong sulfonic acid (super acid). The manufacturing of alternative organic anions, such as imide anions or methide anions that are substituted with electron-withdrawing groups have been disclosed. See for example U.S. Pat. Nos. 5,874,616, 5,273,840 and 5,554,664. In particular, an organic anion having the formula $(R_fSO_2)_2N^-$ or $(R_fSO_2)_3C^-$, wherein $R_f$ is fluorinated alkyl chain, has been used as PAG counter anion. For example, the sulfonium salts or iodonium salts of highly fluorinated imide or methide anion were used as PAG component in 193 nm resist formulations (see for example M. Padmanaban et. al., SPIE, 2003, vol. 5039, p. 723). However, the high fluorine content of the above mentioned methide anion imparts undesired environmental impact due to their limited biodegradability. In addition, the hydrophobic fluorinated chains impart low surface energy which can lead to uneven distribution of the PAG through the depth of the photoresist film. The later PAG non-homogeneous distribution can severely affect the lithographic imaging outcome. Attempts have been made to enable the use of fluorine-free PAGs in photoresist compositions. See, for example, U.S. Pat. No. 7,655,379 and U.S. Patent Application Publication Nos. 2009/0176175, 2009/0181319 and 2009/0181320. However, these attempts did not address critical PAG structural features and physical properties. In particular, the prepared PAG anions lack structural features that are essential for reducing the acid diffusion length during lithographic processing, such as the incorporation of bulky group or functional groups that are prone to non-bonding interactions with other photoresist components. In addition, these PAG anions include fused aromatic or heteroaromatic groups, which are 1) characterized by strong absorption at deep ultraviolet radiation and 2) render the PAG poorly soluble in typical formulation solvents, particularly in polar solvents such as propyleneglycol monomethyl ether (PGME) or propyleneglycol monomethyl acetate (PGMEA).

Thus, there remains a need for PAG anions that are free of perfluoralkylsulfonate, that possess certain structural, chemical and physical characteristics to limit photoacid diffusion rate, provide better miscibility with other photoresist components, and produce super acid upon photodecomposition.

SUMMARY

An embodiment provides photoresist composition, including:
an acid-sensitive polymer,
a solvent, and
a photoacid generator compound having Formula (I):

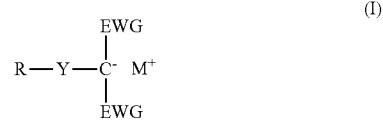

wherein:
EWG is an electron-withdrawing group;
Y is a single bond or a linking group;
R is hydrogen, a straight chain or branched $C_{1-20}$ alkyl group, a straight chain or branched $C_{2-20}$ alkenyl group, a monocyclic or polycyclic $C_{3-20}$ cycloalkyl group, a monocyclic or polycyclic $C_{3-20}$ cycloalkenyl group, a monocyclic or polycyclic $C_{3-20}$ heterocycloalkyl group; a monocyclic or polycyclic $C_{3-20}$ heterocycloalkenyl group; a monocyclic or polycyclic $C_{6-20}$ aryl group, a monocyclic or polycyclic $C_{1-20}$ heteroaryl group, each of which except hydrogen is substituted or unsubstituted, wherein when R comprises a polymerizable group, the photoacid generator is a polymerized unit of the acid-sensitive polymer; and
$M^+$ is an organic cation.

Another embodiment provides a photoresist composition including an acid-sensitive polymer, which is a polymerization product of the photoacid generator compound, and a solvent.

Another embodiment provides a coated substrate, including: (a) a substrate having one or more layers to be patterned on a surface thereof; and (b) a layer of the photoresist composition over the one or more layers to be patterned.

Yet another embodiment provides a method of forming an electronic device, including: (a) applying a layer of the photoresist composition on a substrate; (b) patternwise exposing the photoresist composition layer to activating radiation; and (c) developing the exposed photoresist composition layer to provide a resist relief image.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present inventive concept. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third, etc., may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, when a definition is not otherwise provided, the term "alkyl group" refers to a group derived from a straight or branched chain saturated aliphatic hydrocarbon having the specified number of carbon atoms and having a valence of at least one.

As used herein, when a definition is not otherwise provided, the term "fluoroalkyl group" refers to an alkyl group in which at least one hydrogen atom is replaced with a fluorine atom.

As used herein, when a definition is not otherwise provided, the term "alkoxy group" refers to "alkyl-O—", wherein the term "alkyl" has the same meaning as described above.

As used herein, when a definition is not otherwise provided, the term "fluoroalkoxy group" refers to an alkoxy group in at least one hydrogen atom is replaced with a fluorine atom.

As used herein, when a definition is not otherwise provided, the term "alkenyl group" refers to a group derived from a straight or branched chain unsaturated aliphatic hydrocarbon having the specified number of carbon atoms and having a valence of at least one.

As used herein, when a definition is not otherwise provided, the term "fluoroalkylene group" refers to an alkylene group in which at least one hydrogen atom is replaced with a fluorine atom.

As used herein, when a definition is not otherwise provided, the term "cycloalkyl group" refers to a monovalent group having one or more saturated rings in which all ring members are carbon.

As used herein, when a definition is not otherwise provided, the term "fluorocycloalkyl group" refers to a cycloalkyl group in which at least one hydrogen atom is replaced with a fluorine atom.

As used herein, when a definition is not otherwise provided, the term "heterocycloalkyl group" refers to a monovalent saturated cyclic group that has atoms of at least two different elements as members of its ring(s), one of which is carbon.

As used herein, when a definition is not otherwise provided, the term "heterocycloalkyl group" refers to a monovalent unsaturated cyclic group that has atoms of at least two different elements as members of its ring(s), one of which is carbon.

As used herein, when a definition is not otherwise provided, the term "aryl", which is used alone or in combination, refers to an aromatic hydrocarbon containing at least one ring and having the specified number of carbon atoms. The term "aryl" may be construed as including a group with an aromatic ring fused to at least one cycloalkyl ring.

As used herein, when a definition is not otherwise provided, the term "fluoroaryl group" refers to an aryl group in which at least one hydrogen atom is replaced with a fluorine atom.

As used herein, when a definition is not otherwise provided, the term "aralkyl group" refers to a substituted or unsubstituted aryl group covalently linked to an alkyl group that is linked to a compound, wherein the terms "aryl" and "alkyl" have the same meaning as described above.

As used herein, when a definition is not otherwise provided, the term "fluoroaralkyl group" refers to an aralkyl group in which at least one hydrogen atom is replaced with a fluorine atom.

As used herein, when a definition is not otherwise provided, the term "heteroaryl", which is used alone or in combination, refers to an aromatic hydrocarbon containing at least one ring that has atoms of at least two different elements as members of its ring(s), one of which is carbon, and having the specified number of carbon atoms.

As used herein, when a definition is not otherwise provided, the term "fluoroheteroaryl group" refers to a fluoroheteroaryl group in which at least one hydrogen atom is replaced with a fluorine atom.

As used herein, when a definition is not otherwise provided, the term "substituted" means including at least one substituent such as a halogen (F, Cl, Br, I), hydroxyl, amino, thiol, carboxyl, carboxylate, ester (including acrylates, methacrylates, and lactones), amide, nitrile, sulfide, disulfide, nitro, $C_{1-20}$ alkyl, $C_{1-20}$ cycloalkyl (including adamantyl), $C_{1-20}$ alkenyl (including norbornenyl), $C_{1-20}$ alkoxy, $C_{2-20}$ alkenoxy (including vinyl ether), $C_{6-30}$ aryl, $C_{6-30}$ aryloxy, $C_{7-30}$ alkylaryl, or $C_{7-30}$ alkylaryloxy.

When a group containing a specified number of carbon atoms is substituted with any of the groups listed in the preceding paragraphs, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{20}$ alkyl" refers to a $C_1$-$C_{20}$ alkyl group substituted with $C_6$-$C_{30}$ aryl group, the total number of carbon atoms in the resulting aryl substituted alkyl group is $C_7$-$C_{50}$.

As used herein, when the definition is not otherwise provided, the term "mixture" refers to any combination of the ingredients constituting the blend or mixture without regard to a physical form.

Disclosed herein is a photoresist composition including
an acid-sensitive polymer,
a solvent, and
a photoacid generator compound having Formula (I):

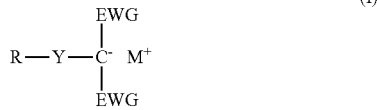

(I)

In Formula (I), EWG may be an electron-withdrawing group, which group that draws electron density from neighboring atoms towards itself by a resonance effect, an inductive effect, a hyperconjugation effect, or a combination thereof. EWG may be a weakly electron-withdrawing group, such as halogen, a moderately electron-withdrawing, such as aldehyde (—CHO), ketone (—COR), carboxylic acid (—CO$_2$H), ester (—CO$_2$R), or amide (—CONH$_2$), or a strongly deactivating group, such as trihalide (—CF$_3$, —CCl$_3$), cyano (—CN), sulfone (—SO$_2$R), sulfonate (—SO$_3$H), or nitro (—NO$_2$). For example, EWG may be an electron-withdrawing group selected from —CN, —NO$_2$, —C(═O) $R^{21}$, —C(═O)OR$^{22}$, and —SO$_2$R$^{23}$, wherein $R^{21}$, $R^{22}$, or $R^{23}$ are each independently a $C_{1-30}$ aliphatic organic group, a $C_{6-30}$ aromatic organic group, or a $C_{1-30}$ heteroaromatic organic group. In an embodiment, EWG may be a cyano group.

In Formula (I), Y may be a linker connecting group R with the anionic center. Y may be a single bond or a linking group. The linking group may include carbon, and may optionally include one or more heteroatoms. In an example, Y may be a single bond, a $C_{1-30}$ linking group, an ether group, a carbonyl group, an ester group, a carbonate group, an amine group, an amide group, a urea group, a sulfate group, a sulfone group, a sulfoxide group, an N-oxide group, a sulfonate group, a sulfonamide group, or a combination of at least two of the foregoing. In another example, Y may be a $C_{1-30}$ linking group optionally including a heteroatom containing O, S, N, F, or a combination of at least one of the foregoing heteroatoms. In still another example, Y may be a single bond, —C(R$^{30}$)$_2$—, —N(R$^{31}$)—, —O—, —S—, —S(═O)$_2$—, —(C═O)—, or a combination thereof, wherein each $R^{30}$ and $R^{31}$ is independently hydrogen or a $C_{1-6}$ alkyl group.

In Formula (I), R may be hydrogen, a straight chain or branched $C_{1-20}$ alkyl group, a straight chain or branched $C_{2-20}$ alkenyl group, a monocyclic or polycyclic $C_{3-20}$ cycloalkyl group, a monocyclic or polycyclic $C_{3-20}$ cycloalkenyl group, a monocyclic or polycyclic $C_{3-20}$ heterocycloalkyl group; a monocyclic or polycyclic $C_{3-20}$ heterocycloalkenyl group; a monocyclic or polycyclic $C_{6-20}$ aryl group, or a monocyclic or polycyclic $C_{1-20}$ heteroaryl group, each of which except hydrogen may be substituted or unsubstituted. In an embodiment, R may be a bulky hydrocarbon group, such as a substituted or unsubstituted polycyclic $C_{3-20}$ cycloalkyl group.

When R comprises a polymerizable group, for example, a straight chain or branched $C_{2-20}$ alkenyl group, a monocyclic or polycyclic $C_{3-20}$ cycloalkenyl group, or a monocyclic or polycyclic $C_{3-20}$ heterocycloalkenyl group; the photoacid generator may be a polymerized unit of the acid-sensitive polymer.

In Formula (I), M$^+$ may be an organic cation, for example, an organic sulfonium cation or an organic iodonium cation.

In an embodiment, the photoacid generator compound may be represented by Formulae (II) and (III):

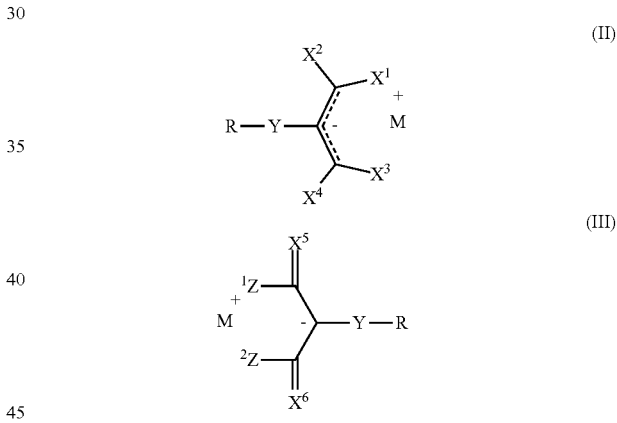

Formula (II) may be represented by the following resonance Formulae (IIa) and (IIb):

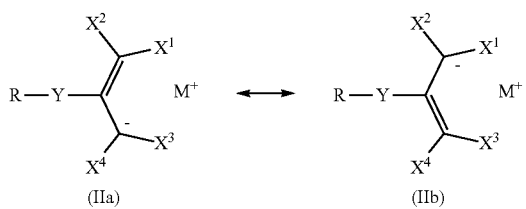

While not wishing to be bound by theory, it is understood that the negative charge in the anion of Formula (II) is stabilized by the double bond and is delocalized between carbon atoms bearing groups $X^1$, $X^2$ and $X^3$, $X^4$, respectively.

In Formula (II), $X^1$, $X^2$, $X^3$ and $X^4$ may each independently be an electron-withdrawing group selected from —F, —CN, —NO$_2$, —C(═O)R$^{24}$, —C(═O)OR$^{25}$, —SO$_2$R$^{26}$, and $CR_f$, wherein $R^{24}$, $R^{25}$, and $R^{26}$ may each independently be a $C_{1-30}$ aliphatic organic group, a $C_{6-30}$ aromatic organic group, or a $C_{1-30}$ heteroaromatic organic group, and $R_f$ may be a $C_1$-$C_{30}$ fluoroalkyl group.

In Formula (II), R may be hydrogen, a straight chain or branched $C_{1-20}$ alkyl group, a straight chain or branched $C_{2-20}$ alkenyl group, a monocyclic or polycyclic $C_{3-20}$ cycloalkyl group, a monocyclic or polycyclic $C_{3-20}$ cycloalkenyl group, a monocyclic or polycyclic $C_{3-20}$ heterocycloalkyl group; a monocyclic or polycyclic $C_{3-20}$ heterocycloalkenyl group; a monocyclic or polycyclic $C_{6-20}$ aryl group, or a monocyclic or polycyclic $C_{1-20}$ heteroaryl group, each of which except hydrogen may be substituted or unsubstituted. In an embodiment, R may be a bulky hydrocarbon group, such as a substituted or unsubstituted polycyclic $C_{3-20}$ cycloalkyl group, which may or may not contain fused cyclic rings. When the polycyclic $C_{3-20}$ cycloalkyl group contains fused cyclic rings, the polycyclic $C_{3-20}$ cycloalkyl group may be derived from a caged hydrocarbon, such as adamantane. Thus, in an embodiment, $R^1$ may be a substituted or unsubstituted adamantyl group, for example, a hydroxyadamantyl group.

In another embodiment, R may be a polymerizable group such as a $C_{2-20}$ alkenyl group. When linker Y includes an oxycarbonyl group —C(=O)O—, the photoacid generator may contain an acrylate or a methacrylate moiety.

In Formula (II), Y may be a linker connecting group R with the anionic center. Y may be a single bond or a linking group. The linking group may include carbon, and may optionally include one or more heteroatoms. In an example, Y may be a single bond, a $C_{1-30}$ linking group, an ether group, a carbonyl group, an ester group, a carbonate group, an amine group, an amide group, a urea group, a sulfate group, a sulfone group, a sulfoxide group, an N-oxide group, a sulfonate group, a sulfonamide group, or a combination of at least two of the foregoing. In another example, Y may be a $C_{1-30}$ linking group optionally including a heteroatom containing O, S, N, F, or a combination of at least one of the foregoing heteroatoms. In still another example, Y may be a single bond, —C($R^{30}$)$_2$—, —N($R^{31}$)—, —O—, —S—, —S(=O)$_2$—, —(C=O)—, or a combination thereof, wherein each $R^{30}$ and $R^{31}$ is independently hydrogen or a $C_{1-6}$ alkyl group.

Each "=" represents a partial double bond.

In Formula (I), $M^+$ may be an organic cation. For example, $M^+$ may be an organic sulfonium cation or an organic iodonium cation.

The photoacid generator having Formula (I) may have the following structures:

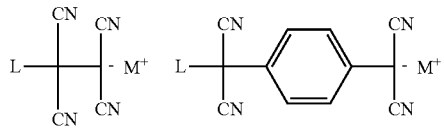

wherein L is an organic substituent and $M^+$ is an organic cation.

The photoacid generator having Formula (I) may include no halogen atoms.

Specific examples of PAGs having Formula (II) are shown below:

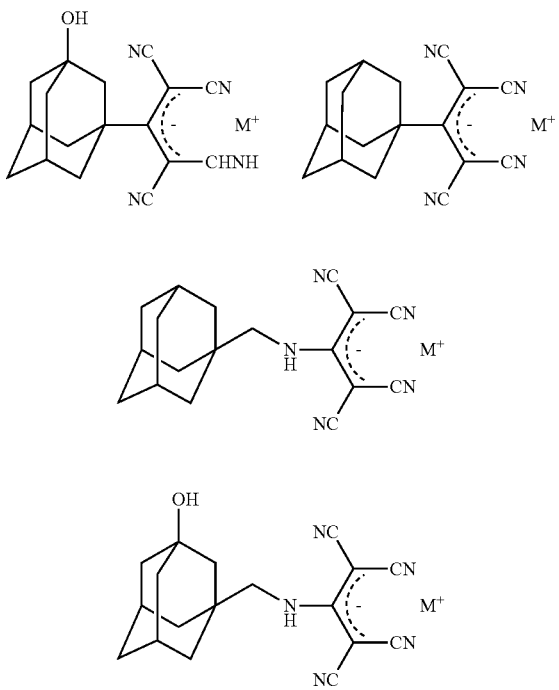

The photoacid generators of the present invention may be covalently bound to a polymer, wherein the polymer contains one or more acid sensitive structural units. Thus, an embodiment provides an acid-sensitive polymer, which is a polymerization product of the photoacid generator compound. For an ionic acid generator, either cation or anion components may be covalently linked to a polymer. Alternatively, both the cation and the anion components may be covalently bound to the polymer.

For instance, the photoacid generator anion component may include a polymerizable group (such as acrylate, methacrylate, vinyl ether) which can be reacted with a pre-formed polymer, or other monomers, to provide a polymer-bound acid generator. Exemplary polymerizable photoacid generator anion components include the following structures:

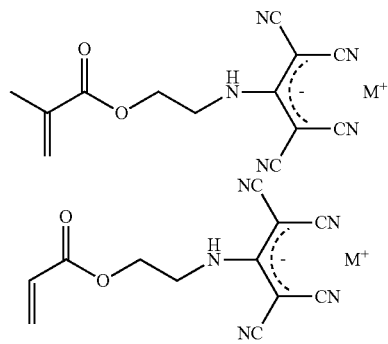

In another embodiment, the photoacid generator may be represented by Formula (III):

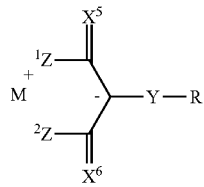
(III)

In Formula (III), $X^5$ and $X^6$ may each independently be an oxygen atom, an electron withdrawing group selected from divalent groups $C(CN)_2$, $C(NO_2)_2$, $C(COR^{27})_2$, $C(CO_2R^{28})_2$, $C(SO_2R^{29})_2$, and $C(R_f)_2$, wherein $R_f$ is a $C_1$-$C_{30}$ fluoroalkyl group.

Y, R, and M may be the same as in Formula (I) above.

$Z^1$ and $Z^2$ may each independently be hydrogen, a straight chain or branched $C_{1-50}$ alkyl group, a monocyclic or polycyclic $C_{3-50}$ cycloalkyl group, a monocyclic or polycyclic $C_{3-50}$ heterocycloalkyl group; a monocyclic or polycyclic $C_{6-50}$ aryl group, a monocyclic or polycyclic $C_{5-20}$ heteroaryl group, or a combination thereof. Groups $Z^1$ and $Z^2$ may be optionally connected to each other to form a ring.

In Formula (III),
$X^5$ and $X^6$ may each be $C(CN)_2$;
R may be hydrogen; and
Y may be a single bond.

At least one of R, $Z^1$, and $Z^2$ may include a polymerizable group such as a $C_{2-20}$ alkenyl group. When linker Y includes an oxycarbonyl group —C(=O)O—, the photoacid generator may contain an acrylate or a methacrylate moiety.

Examples of photoacid generators represented by Formula (III) may include the following compounds:

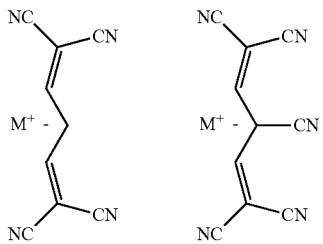

In Formula (III), when R is hydrogen, Y is a single bond, $Z^1$ and $Z^2$ are connected together to form $C_{5-20}$ monocyclic or polycyclic aliphatic or aromatic group, a photoacid generator having Formula (III) may be represented by Formula (IV):

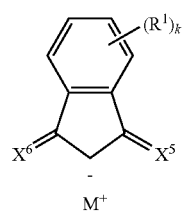
(IV)

In Formula (IV), $X^5$ and $X^6$ may be the same as in Formula (III) and $R^1$ may be a halogen, an electron-withdrawing group such as a nitro group, a cyano group, a sulfonyl group, or a fluorine atom, a $C_{1-10}$ alkyl group, a $C_{1-10}$ fluoroalkyl group, a $C_{1-10}$ alkoxy group, a $C_{1-10}$ fluoroalkoxy group, a $C_{3-10}$ cycloalkyl group, a $C_{3-10}$ fluorocycloalkyl group, a $C_{3-10}$ cycloalkoxy group, a $C_{3-10}$ fluorocycloalkoxy group, or an electron-withdrawing group selected from $NO_2$, CN, $C(R_f)_3$ or $CO_2R$, wherein $R_f$ is a $C_1$-$C_{30}$ fluoroalkyl group; and k may be an integer of 0, 1, 2, 3, or 4.

Examples of photoacid generators represented by Formula (IV) are shown below:

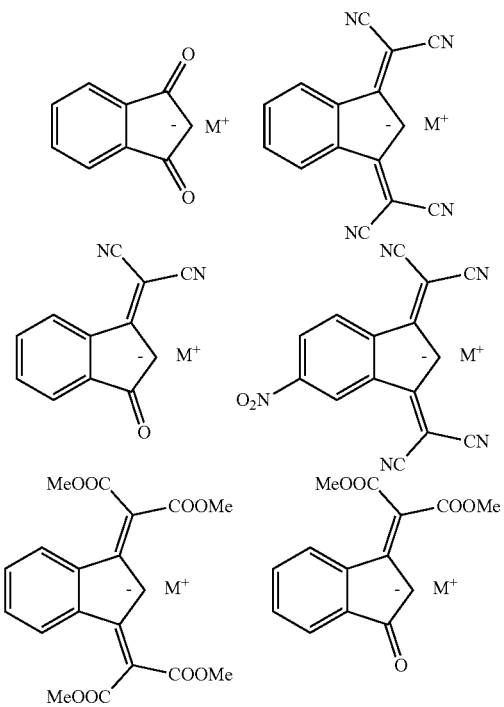

Formulae (I), (II), (III), and (IV) all include a cation $M^+$, which may be an organic cation. For example, $M^+$ may be an organic sulfonium cation or an organic iodonium cation.

In an embodiment, $M^+$ may be an organic cation having Formula (VII):

(VII)

In Formula (VII),
$R^0$ may be a $C_{1-20}$ alkyl group, a $C_{1-20}$ fluoroalkyl group, a $C_{3-20}$ cycloalkyl group, a $C_{3-20}$ fluorocycloalkyl group, a $C_{2-20}$ alkenyl group, a $C_{2-20}$ fluoroalkenyl group, a $C_{6-20}$ aryl group, a $C_{6-20}$ fluoroaryl group, a $C_{1-20}$ heteroaryl group, a $C_{7-20}$ aralkyl group, a $C_{7-20}$ fluoroaralkyl group, a $C_{2-20}$ heteroaralkyl group, or a $C_{2-20}$ fluoroheteroaralkyl group, each of which is substituted or unsubstituted, and Ar is a substituted or unsubstituted $C_{6-30}$ aromatic organic group, wherein Ar is optionally connected to $R^0$.

Specific examples of the organic iodonium cation may be:

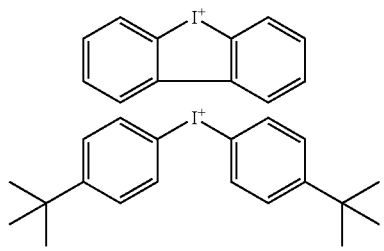

In an embodiment, M$^+$ may be an organic cation having Formula (V):

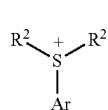
(V)

wherein, each R$^2$ is independently a C$_{1-20}$ alkyl group, a C$_{1-20}$ fluoroalkyl group, a C$_{3-20}$ cycloalkyl group, a C$_{3-20}$ fluorocycloalkyl group, a C$_{2-20}$ alkenyl group, a C$_{2-20}$ fluoroalkenyl group, a C$_{6-20}$ aryl group, a C$_{6-20}$ fluoroaryl group, a C$_{1-20}$ heteroaryl group, a C$_{7-20}$ aralkyl group, a C$_{7-20}$ fluoroaralkyl group, a C$_{2-20}$ heteroaralkyl group, or a C$_{2-20}$ fluoroheteroaralkyl group, each of which is substituted or unsubstituted, wherein each R$^2$ is either separate or connected to the other group R$^2$ via a single bond or a linking group to form a ring, and Ar is a substituted or unsubstituted C$_{6-30}$ aromatic organic group.

In another embodiment, M$^+$ may be an organic cation having Formula (VI):

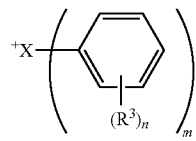
(VI)

wherein

X is I or S;

each R$^3$ is independently a halogen, —CN, —OH, a C$_{1-10}$ alkyl group, a C$_{1-10}$ fluoroalkyl group, a C$_{1-10}$ alkoxy group, a C$_{1-10}$ fluoroalkoxy group, a C$_{3-10}$ cycloalkyl group, a C$_{3-10}$ fluorocycloalkyl group, a C$_{3-10}$ cycloalkoxy group, a C$_{3-10}$ fluorocycloalkoxy group, or a C$_{6-10}$ alkoxycarbonylalkyleneoxy group;

each n is an integer of 0, 1, 2, 3, 4, and 5; and m is an integer of 2 or 3, provided that when X is I, m is 2, and where X is S, m is 3.

In still another embodiment, X may be iodine (I) and at least one n may not be 0. In this embodiment, an iodonium cation requires that at least one substituent is present at the aromatic ring.

In yet another embodiment, M$^+$ may be an organic cation having Formulae (VII) or (VIII):

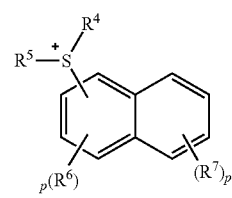
(VII)

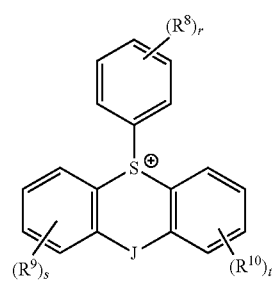
(VIII)

wherein

R$^4$, R$^5$, R$^6$, R$^7$, R$^8$, R$^9$, and R$^{10}$ are each independently a halogen, —CN, —OH, a C$_{10}$ alkyl group, a C$_{1-10}$ fluoroalkyl group, a C$_{1-10}$ alkoxy group, a C$_{1-10}$ fluoroalkoxy group, a C$_{3-10}$ cycloalkyl group, a C$_{3-10}$ fluorocycloalkyl group, a C$_{3-10}$ cycloalkoxy group, or a C$_{3-10}$ fluorocycloalkoxy group, each of which except a halogen, —CN, and —OH may be substituted or unsubstituted;

J is a single bond or a connecting group selected from S, O, and C=O, p is each independently an integer of 0, 1, 2, 3, or 4;

r is an integer of 0, 1, 2, 3, 4, and 5, and s and t are each independently an integer of 0, 1, 2, 3, and 4.

R$^3$ in Formula (VI), R$^6$ and R$^7$ in Formula (VII), and R$^8$, R$^9$ and R$^{10}$ in Formula (VIII) may optionally comprise an acid cleavable group, for example, a C$_{6-10}$ alkoxycarbonylalkyleneoxy group. An example of a C$_{6-10}$ alkoxycarbonylalkyleneoxy group is t-butyloxycarbonylmethoxy group as shown in the following compounds:

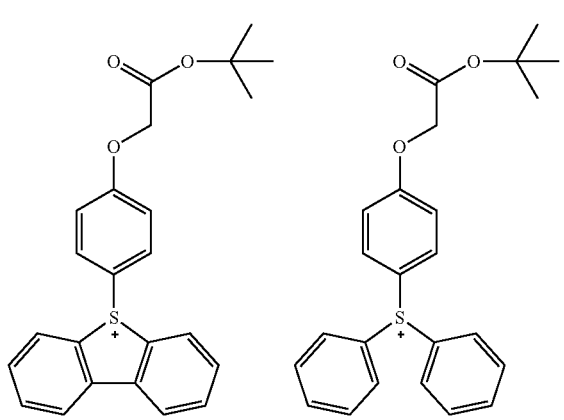

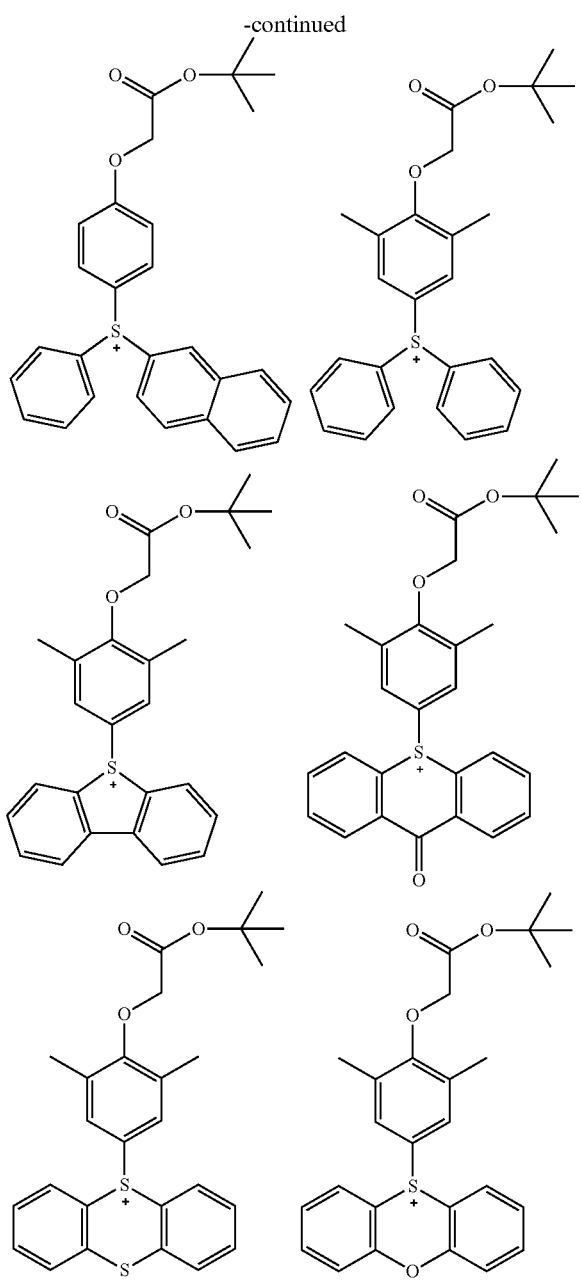

The present inventive concept provides photoacid generators that include new methide type anions. Unlike known methide anions that are substituted with three electron-withdrawing perfluorosulfonyl groups, methides of this disclosure include one or more electron-withdrawing substituents and at least one functional substituent. The functional substituent is designed to impart specific structural and physical features that are not present in known methide structures. For example, the new design allows the substitution of the methide anion with 193 nanometer (nm) transparent and bulky cycloaliphatic groups, such adamantanyl (adamantyl) or substituted adamantanyl (for example, hydroxyadamantyl). Incorporating bulky cycloaliphatic groups in PAG anions enhances miscibility of the corresponding PAG with 193 nm type polymer matrix and leads to slower diffusion during lithographic processing. The inventive concept allows functionalization of methide anion with a polymerizable group. Notably, known methide anions in the art are limited to $(R_fSO_2)_3C^-$ electron withdrawing substituent (wherein $R_f$ is a fluoroalkyl group). The present inventive concept allows the substitutions with a wide range of electron-withdrawing group, including fluorine-free electron-withdrawing groups.

The generated photoacids are expected to possess high activation energy of diffusion during lithographic processing due to the strong non-bonding interaction of the photoacid functional groups with other photoresist components. For instance, the nitrogen atom of electron withdrawing cyano group is prone to hydrogen bonding with variety of hydrogen bond donor groups which are present on the photoresist matrix.

The photoacid generator may be formulated with or combined with a copolymer and a solvent to form a photoresist composition. Where the combination is a polymer bound photoacid generator, an appropriately functionalized photoacid generator can be copolymerized with one or more monomers to form the copolymer, or the photoacid generator can be grafted onto the copolymer.

A copolymer useful for forming a photoresist in combination with the photoacid generator disclosed herein may include an acid-deprotectable (acid-sensitive) monomer, a base-soluble monomer, a dissolution rate modifying monomer, and an etch resistant monomer. Any such monomers or combinations of monomers suitable for forming, for example, a 193 nm photoresist polymer. In an embodiment, a combination of monomers may be used, which include a (meth)acrylate monomer having an acid-deprotectable base soluble group, a (meth)acrylate monomer having a lactone functional group, a (meth)acrylate monomer having a base-soluble group, or a combination including at least one of the foregoing monomers. Other monomers, such as (meth)acrylate monomer for improving adhesion, etch resistance, and so on, may also be included.

Any acid-deprotectable monomer useful for forming a 193 nm photoresist polymer may be used. Exemplary acid-deprotectable monomers include, but are not limited to:

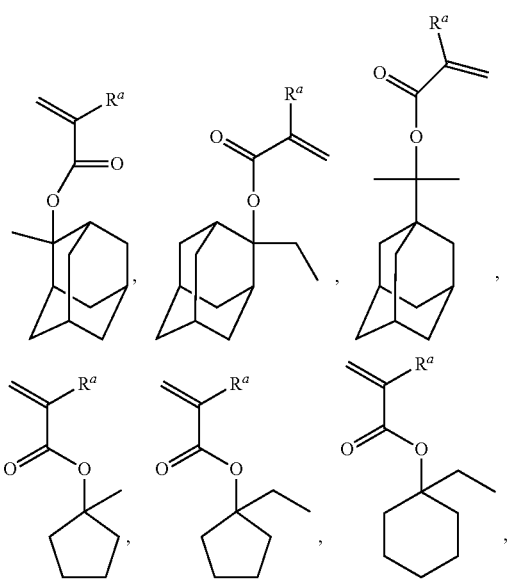

-continued

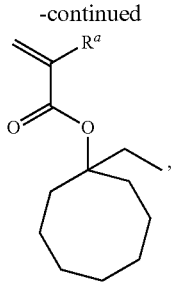

or a combination comprising at least one of the foregoing monomers, wherein $R^a$ is H, F, CN, $C_{1-10}$ alkyl, or $C_{1-10}$ fluoroalkyl.

Any lactone-containing monomer useful for forming a 193 nm photoresist polymer may be used. Exemplary lactone-containing monomers include, but are not limited to:

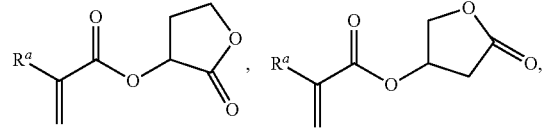

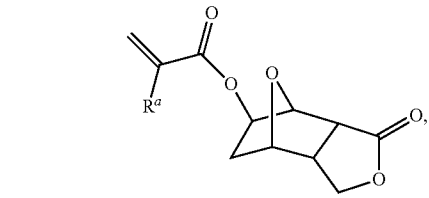

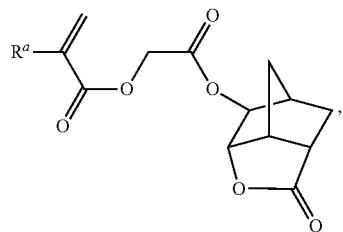

or a combination including at least one of the foregoing monomers, wherein $R^a$ is H, F, CN, a $C_{1-10}$ alkyl group, or a $C_{1-10}$ fluoroalkyl group.

Any base-soluble monomer useful for forming a 193 nm photoresist polymer may be used. Exemplary additional base-soluble (meth)acrylate monomers include, but are not limited to:

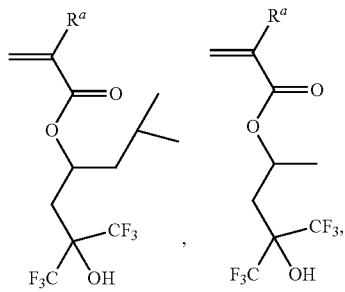

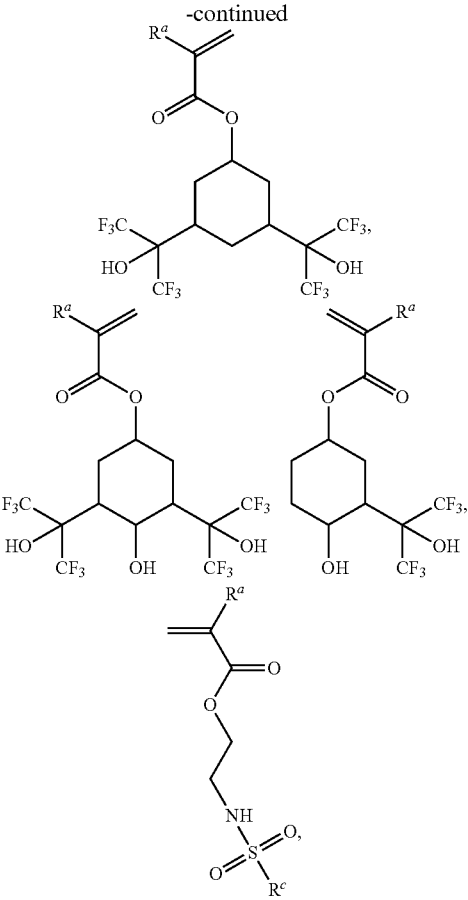

or a combination including at least one of the foregoing monomers, wherein $R^a$ is H, F, CN, a $C_{1-10}$ alkyl group, or a $C_{1-10}$ fluoroalkyl group, and $R^c$ is a $C_{1-4}$ perfluoroalkyl group.

The polymer may also include other monomers, including cage-structured monomers for enhancing etch resistance, with or without functional groups for improving adhesion. An exemplary adhesion-improving monomer may include:

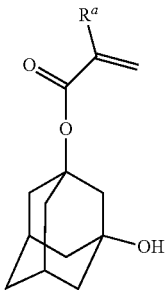

or a combination comprising the foregoing and at least one additional monomer, wherein $R^a$ is H, $C_{1-6}$ alkyl, or $CF_3$.

The photoacid generator may be combined with the copolymer, either in admixture, by copolymerization or both, to form a photoresist. The photoresist may optionally further include a second acid sensitive polymer and/or photoacid generator, an amine or an amide additive to adjust photospeed and/or acid diffusion, a solvent, and a surfactant.

The second acid-sensitive polymer may be any polymer suitable for formulating photoresists for use at 193 nm. Such acid-sensitive polymers may include an acid sensitive polymer including acid sensitive groups and lactone-containing groups, wherein the deprotection of the acid sensitive group on exposure to acid releases a base-soluble group. The acid-sensitive polymer may be a polymer-bound photoacid generator (PBP) wherein the photoacid generator repeat unit is an anion or a cation.

The photoresist composition may further include an amine or amide compound, referred to herein as a quencher. Quenchers may more broadly include, for example, compounds which are hydroxides, carboxylates, amines, imines, and amides. In an embodiment, a useful quencher is an amine, an amide, or a combination comprising at least one of the foregoing. For example, such quenchers may include $C_{1-30}$ organic amines, imines, or amides, or may be a $C_{1-30}$ quaternary ammonium salt of a strong base (for example, a hydroxide or alkoxide) or a weak base (for example, a carboxylate). Exemplary quenchers may include amines such as Troger's base, a hindered amine such as diazabicycloundecene (DBU) or diazabicyclononene (DBN), N-protected amines such as N-t-butylcarbonyl-1,1-bis(hydroxymethyl)-2-hydroxyethylamine (TBOC-TRIS), or ionic quenchers including quaternary alkyl ammonium salts such as tetrabutylammonium hydroxide (TBAH) or tetrabutyl ammonium lactate.

Other components of the photoresist may include solvents and surfactants.

Solvents generally suitable for dissolving, dispensing, and coating the components may include anisole, alcohols including ethyl lactate, methyl 2-hydroxybutyrate (HBM), 1-methoxy-2-propanol (also referred to as propylene glycol methyl ether, PGME), and 1-ethoxy-2 propanol, esters including n-butylacetate, 1-methoxy-2-propyl acetate (also referred to as propylene glycol methyl ether acetate, PGMEA), methoxyethoxypropionate, ethoxyethoxypropionate, and gamma-butyrolactone, ketones including cyclohexanone and 2-heptanone, and a combination comprising at least one of the foregoing solvents.

Surfactants may include fluorinated and non-fluorinated surfactants, and may, for example, be non-ionic. Exemplary fluorinated non-ionic surfactants may include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoacid generator may be present in the photoresist in an amount of 0.01 to 20 percent by weight (wt %), for example, 0.1 to 15 wt %, based on the total weight of solids. Where a polymer bound photoacid generator is used, the polymer bound photoacid generator as the corresponding monomer is present in the same amount. The copolymer may be present in an amount of 50 to 99 wt %, for example, 55 to 95 wt %, in another example, 60 to 90 wt %, and in still another example, 65 to 90 wt % based on the total weight of solids. It will be understood that the term "polymer" used in this context of a component in a photoresist may mean only the copolymer disclosed herein, or a combination of the polymer with another polymer useful in a photoresist. A surfactant may be included in an amount of 0.01 to 5 wt %, for example, 0.1 to 4 wt %, and in another example, 0.2 to 3 wt %, based on the total weight of solids. A quencher may be included in a relatively small amount of for example, from 0.03 to 5 wt % based on the total weight of solids. Other additives such as embedded barrier layer (EBL) materials for immersion lithography applications may be included in amounts of less than or equal to 30 wt %, for example, less than or equal to 20%, or in another example, less than or equal to 10%, based on the total weight of solids. The total solids content for the photoresist composition may be 0.5 to 50 wt %, for example, 1 to 45 wt %, and in another example, 2 to 40 wt %, and still in another example, 5 to 35 wt %, based on the total weight of solids and solvent. It will be understood that the solids may include a copolymer, a photoacid generator, a quencher, a surfactant, and any optional additives, exclusive of solvent.

The photoresist composition disclosed herein may be used to form a film comprising the photoresist composition, where the film on the substrate constitutes a coated substrate. Such a coated substrate may include: (a) a substrate having one or more layers to be patterned on a surface thereof; and (b) a layer of the photoresist composition over the one or more layers to be patterned. For example, patterning may be carried out using ultraviolet radiation at wavelength of less than 248 nm, and in particular, at 193 nm. The patternable film thus includes the photoacid generator of Formula (I).

A method of forming an electronic device therefore includes: (a) applying a layer of a photoresist composition on a substrate; (b) patternwise exposing the photoresist composition layer to activating radiation; and (c) developing the exposed photoresist composition layer to provide a resist relief image. For example, the radiation is 193 nm or 248 nm radiation.

Substrates may be of any dimension and shape, and may, for example, be those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. For example, the surfaces of substrates herein include critical dimension layers to be patterned including, for example, one or more gate-level layers or other critical dimension layer on the substrates for semiconductor manufacture. Such substrates may, for example, include silicon, SOI, strained silicon, and other such substrate materials, formed as circular wafers having dimensions such as, for example, 200 mm, 300 mm, or larger in diameter, or other dimensions useful for wafer fabrication production.

The present inventive concept is further illustrated by the following examples. All compounds and reagents used herein are available commercially except where a procedure is provided below.

EXAMPLES

Example 1: Photoacid Generator PAG 1 is Prepared According to the Synthetic Scheme Outlined in Synthesis Scheme 1

Synthesis Scheme 1

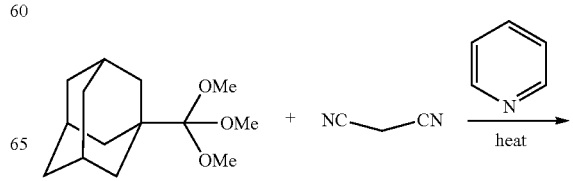

-continued

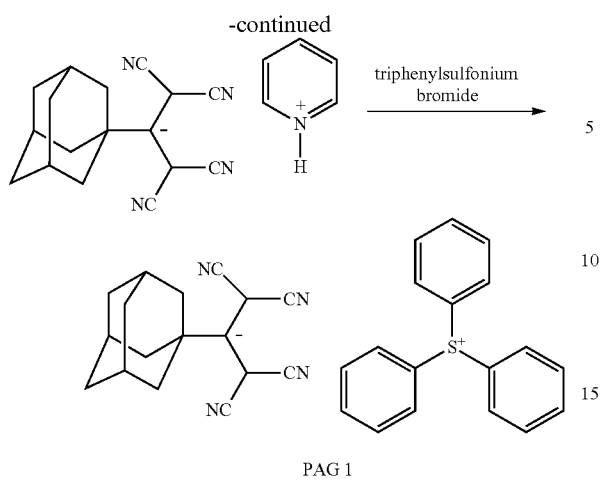

PAG 1

A solution of malononitrile (10.00 grams (g), 151 millimoles (mmol)), 1-(trimethoxymethyl)adamantane (18.19 g, 76 mmol), and pyridine (5.99 g, 76 mmol) is heated under reflux for 20 minutes (min). The reaction mixture is cooled to room temperature. Under agitation, the reaction mixture is charged with dichloromethane (200 milliliters (mL)), triphenylsulfonium bromide (23.38 g, 68 mmol), and deionized water (100 mL). The mixture is stirred at room temperature for 16 h. The organic phase is separated and is washed with three 100 mL volumes of deionized water. Removing the solvent under vacuum produces triphenylsulfonium 2-adamantyl-1,1,3,3-tetracyanopropenide (PAG 1) (36.70 g, 100% yield).

Example 2: Photoacid Generator PAG-2 is Prepared According to the Synthetic Scheme Outlined in Synthesis Scheme 2

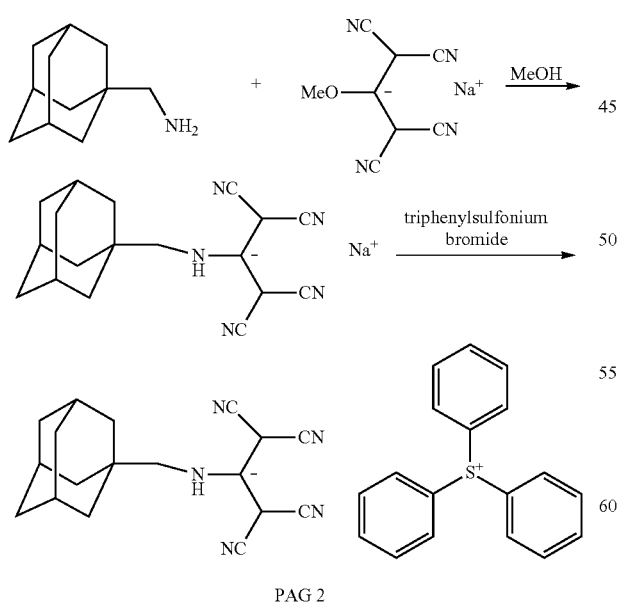

PAG 2

The synthesis of the starting material 2-methoxy-1,1,3,3-tetracyanopropenide is described in *J. Am. Chem. Soc.* 1958, 80, 2795. Sodium 2-methoxy-1,1,3,3-tetracyanopropenide (10.00 g, 51.5 mmol) is dissolved in methanol (100 mL) and adamantylmethylamine (8.51 g, 51.5 mmol) is added thereto. The reaction mixture is heated under reflux for two hours and cooled to ambient temperature. The solvent is removed under vacuum. To the residual solid triphenylsulfonium bromide (15.91 g, 46.4 mmol), dichloromethane (150 mL), and deionized water (75 mL) are added. The mixture is stirred for 16 hours. The organic phase is separated and washed with three 75 mL volumes of deionized water. The solvent is removed under vacuum to give triphenylsulfonium 2-adamantylmethylamino-1,1,3,3-tetracyanopropenide (PAG 2) (26.34 g, 100% yield).

Example 3: Photoacid Generator PAG 3 is Prepared by the Synthetic Scheme Outlined in Scheme 3

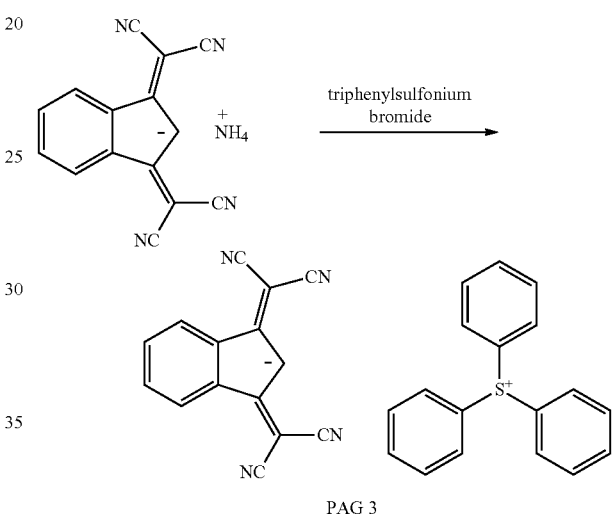

PAG 3

The starting material 1,3-bis(dicyanomethylene)-2,3-dihydro-1H-inden-2-ide ammonium is prepared according to literature procedure (*J. Org. Chem.*, 2013, 78(3), 1014) and is mixed with equimolar amount of triphenylsulfonium bromide in a mixture of water/methylene chloride 1/1 by volume. The mixture is stirred for 16 hours. The organic phase is separated and washed with three times with deionized water. The solvent is removed under vacuum to give PAG 3.

Example 4: Photoacid Generator PAG 4 is Prepared by the Synthetic Scheme Outlined in Scheme 4

Synthesis Scheme 4

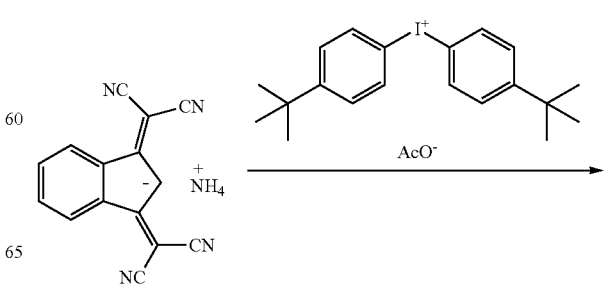

-continued

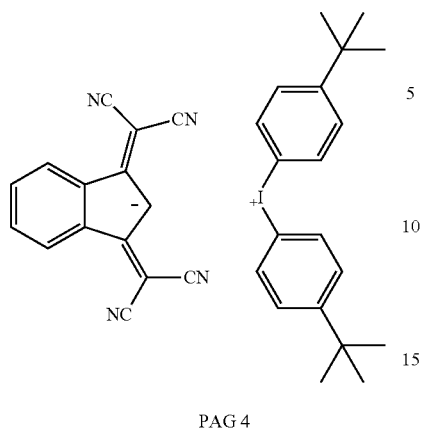

PAG 4

The starting material 1,3-bis(dicyanomethylene)-2,3-dihydro-1H-inden-2-ide ammonium is prepared according to literature procedure (*J. Org. Chem.*, 2013, 78(3), 1014) and is mixed with equimolar amount of di-(4-t-butylphenyl) iodonium acetate in a mixture of water/methylene chloride 1/1 by volume. The mixture is stirred for 16 hours. The organic phase is separated and washed with three times with deionized water. The solvent is removed under vacuum to give PAG 4.

Example 5: Lithographic Evaluation

The photoacid generators are evaluated lithographically according to the following procedure. Photoresists are formulated using the components and proportions shown in Table 1. The commercial photoresist polymer A2 is used in all examples. Polymer A2 is a pentapolymer incorporating monomers M1, M2, M3, M4, and M5 shown below, where the mole percentage of M1/M2/M3/M4/M5 is 20/20/30/20/10 for a total of 100 mole percent of monomers. The molecular weight (Mw) of the polymer was 8,000 grams per mole (g/mol). The PAG, base (t-butyloxycarbonyl-4-hydroxypyridine, TBOC-4HP), and surface leveling agent (surfactant) PF 656, available from Omnova, are in weight percent based on 100% solids content, with the balance of the solids being the polymer. The solvents used in these formulations are PGMEA (S1) and HBM (S2). The final content of solids in both examples were 4 percent by weight (wt %). The weight ratio of solvent S1:S2 in the final formulation was 1:1. Photoresist formulation compositions for Comparative Example and Examples A, B and C are shown in Table 1 below:

M1

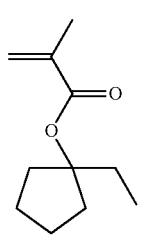

M2

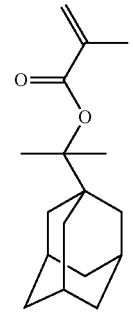

M3

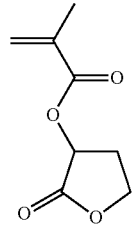

M4

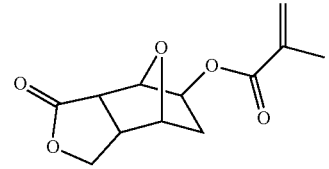

M5

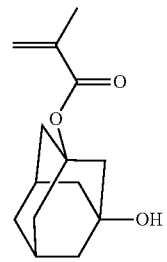

TABLE 1

| Sample | PAG | PAG (wt %) | Base (wt %) | SLA (wt %) |
| --- | --- | --- | --- | --- |
| Comparative Example | Triphenylsulfonium perfluorobutane-sulfonate | 9.56 | 1.03 | 0.1 |
| Example A | PAG 1 | 9.18 | 1.03 | 0.1 |
| Example B | PAG 2 | 9.68 | 1.03 | 0.1 |
| Example C | PAG 3 | 8.56 | 1.03 | 0.1 |

The above photoresists were lithographically processed as follows. The photoresist was spin coated onto a 200 millimeter (mm) silicon wafer having 84 nm of an organic antireflective coating (AR™ 77, Dow Electronic Materials) and baked at 110° C. for 60 seconds, to form a resist film 100 nm in thickness. The photoresist was exposed with ArF excimer laser (193 nm) through a mask pattern targeting a line and space pattern (L/S pattern) having a line width of 90 nm and a pitch of 180 nm, using an ArF exposure apparatus ASML-1100 (manufactured by ASML), NA (numerical aperture)=0.75 under annular illumination with outer/inner sigma of 0.89/0.64 with focus offset/step 0.10/0.05. The wafers were post exposure baked (PEB) at 1000° C. for 60 seconds followed by developing with 0.26 normal (N) aqueous tetramethylammonium hydroxide (TMAH) developer and subsequent water wash.

In each example, an L/S pattern having a line width of 90 nm and a pitch of 180 nm was formed. Mask Error Factor (MEF) and Exposure Latitude (EL) were determined by processing the image captured by top-down scanning electron microscopy (SEM) using a Hitachi 9380 CD-SEM, operating at an accelerating voltage of 800 volts (V), probe current of 8.0 picoamperes (pA), using 200 Kx magnification. Exposure latitude (EL) was defined as a difference in exposure energy to print +/−10% of the target diameter normalized by the sizing energy. Mask Error Factor (MEF) was defined as the ratio of CD change on the resolved resist pattern to the relative dimension change on the mask pattern.

The results from the lithographic evaluation of the above photoresist formulations shows that Examples B, C and D, which utilizes the PAG 1, PAG 2 and PAG 3 respectively, show the improved lithographic performance of greater exposure latitude, and improved mask error factor.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A photoresist composition, comprising:
an acid-sensitive polymer,
a solvent, and
a photoacid generator compound having Formula (I):

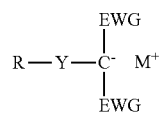

(I)

wherein:
each EWG is independently chosen from —CN, —NO$_2$, —C(=O)R$^{21}$, —C(=O)OR$^{22}$, or —SO$_2$R$^{23}$, wherein R$^{21}$, R$^{22}$, or R$^{23}$ are each independently a C$_{1-30}$ aliphatic organic group, a C$_{6-30}$ aromatic organic group, or a C$_{1-30}$ heteroaromatic organic group;

Y is a single bond or a linking group;

R is hydrogen, a straight chain or branched C$_{1-20}$ alkyl group, a straight chain or branched C$_{2-20}$ alkenyl group, a monocyclic or polycyclic C$_{3-20}$ cycloalkyl group, a monocyclic or polycyclic C$_{3-20}$ cycloalkenyl group, a monocyclic or polycyclic C$_{3-20}$ heterocycloalkyl group; a monocyclic or polycyclic C$_{3-20}$ heterocycloalkenyl group; a monocyclic or polycyclic C$_{6-20}$ aryl group, or a monocyclic or polycyclic C$_{1-20}$ heteroaryl group, each of which except hydrogen is substituted or unsubstituted, wherein when R comprises a polymerizable group, the photoacid generator is a polymerized unit of the acid-sensitive polymer; and M$^+$ is an organic cation.

2. A photoresist composition comprising:
an acid-sensitive polymer,
a solvent, and
a photoacid generator compound having Formula (III):

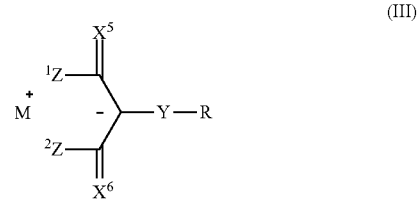

(III)

wherein:
X$^5$ and X$^6$ are each independently an electron withdrawing group selected from C(NO$_2$)$_2$, C(COR$^{21}$)$_2$, C(CO$_2$R$^{22}$)$_2$, C(SO$_2$R$^{23}$)$_2$, and C(R$_f$)$_2$, wherein R$^{21}$, R$^{22}$, and R$^{23}$ are each independently a C$_{1-30}$ aliphatic organic group, a C$_{6-30}$ aromatic organic group, or a C$_{1-30}$ heteroaromatic organic group, and wherein R$_f$ is a C$_1$-C$_{30}$ fluoroalkyl group;

Z$^1$ and Z$^2$ are each independently hydrogen, a straight chain or branched C$_{1-50}$ alkyl group, a monocyclic or polycyclic C$_{3-50}$ cycloalkyl group, a monocyclic or polycyclic C$_{3-50}$ heterocycloalkyl group; a monocyclic or polycyclic C$_{6-50}$ aryl group, a monocyclic or polycyclic C$_{5-20}$ heteroaryl group, or a combination thereof, wherein groups Z$^1$ and Z$^2$ are optionally connected to each other to form a ring;

Y is a single bond or a linking group;

R is a straight chain or branched C$_{1-20}$ alkyl group, a straight chain or branched C$_{2-20}$ alkenyl group, a monocyclic or polycyclic C$_{3-20}$ cycloalkyl group, a monocyclic or polycyclic C$_{3-20}$ cycloalkenyl group, a monocyclic or polycyclic C$_{3-20}$ heterocycloalkyl group; a monocyclic or polycyclic C$_{3-20}$ heterocycloalkenyl group; a monocyclic or polycyclic C$_{6-20}$ aryl group, or a monocyclic or polycyclic C$_{1-20}$ heteroaryl group, each of which is substituted or unsubstituted, and M$^+$ is an organic cation.

3. A photoresist composition, comprising:
an acid-sensitive polymer,
a solvent, and
a photoacid generator compound having Formula (III):

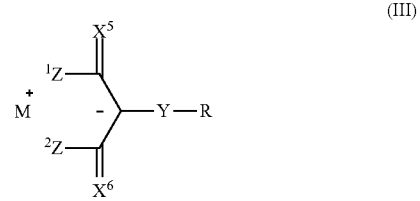

(III)

wherein in Formula (III):
X$^5$ and X$^6$ are each C(CN)$_2$;
Z$^1$ and Z$^2$ are each independently hydrogen, a straight chain C$_{1-50}$ alkyl group, a branched C$_{3-50}$ alkyl group, a monocyclic C$_{3-50}$ cycloalkyl group, a polycyclic C$_{7-50}$ cycloalkyl group, a monocyclic or polycyclic C$_{3-50}$ heterocycloalkyl group; a monocyclic C$_{6-50}$ aryl group, a polycyclic C$_{10-50}$ aryl group, a monocyclic or polycyclic C$_{5-20}$ heteroaryl group, or a combination thereof;

R is a straight chain or branched $C_{1-20}$ alkyl group, a straight chain or branched $C_{2-20}$ alkenyl group, a monocyclic or polycyclic $C_{3-20}$ cycloalkyl group, a monocyclic or polycyclic $C_{3-20}$ cycloalkenyl group, a monocyclic or polycyclic $C_{3-20}$ heterocycloalkyl group; a monocyclic or polycyclic $C_{3-20}$ heterocycloalkenyl group; a monocyclic or polycyclic $C_{6-20}$ aryl group, or a monocyclic or polycyclic $C_{1-20}$ heteroaryl group, each of which is substituted or unsubstituted;

Y is a single bond or a linking group; and $M^+$ is an organic cation.

4. The photoresist composition of claim 2, wherein in Formula (III):

Y is a single bond.

5. A photoresist composition comprising:
an acid-sensitive polymer,
a solvent, and
a photoacid generator compound having Formula (IV):

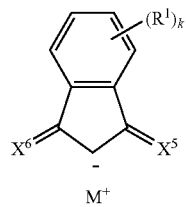

(IV)

wherein, $X^5$ and $X^6$ are each independently an electron withdrawing group selected from $C(NO_2)_2$, $C(COR^{27})_2$, $C(CO_2R^{28})_2$, $C(SO_2R^{29})_2$, and $C(R_f)_2$, wherein $R^{27}$, $R^{28}$, and $R^{29}$ are each independently a $C_{1-30}$ aliphatic organic group, a $C_{6-30}$ aromatic organic group, or a $C_{1-30}$ heteroaromatic organic group, and wherein $R_f$ is a $C_1$-$C_{30}$ fluoroalkyl group;

$M^+$ is an organic cation;

$R^1$ is a halogen, a $C_{1-10}$ alkyl group, a $C_{1-10}$ fluoroalkyl group, a $C_{1-10}$ alkoxy group, a $C_{1-10}$ fluoroalkoxy group, a $C_{3-10}$ cycloalkyl group, a $C_{3-10}$ fluorocycloalkyl group, a $C_{3-10}$ cycloalkoxy group, a $C_{3-10}$ fluorocycloalkoxy group, or an electron-withdrawing group selected from $NO_2$, $CN$, $C(R_f)_3$ or $CO_2R$, wherein $R_f$ is a $C_1$-$C_{30}$ fluoroalkyl group; and k is an integer of 0, 1, 2, 3, or 4.

6. The photoresist composition of claim 1, wherein $M^+$ is an organic cation having Formula (V):

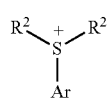

(V)

wherein, each $R^2$ is independently a $C_{1-20}$ alkyl group, a $C_{1-20}$ fluoroalkyl group, a $C_{3-20}$ cycloalkyl group, a $C_{3-20}$ fluorocycloalkyl group, a $C_{2-20}$ alkenyl group, a $C_{2-20}$ fluoroalkenyl group, a $C_{6-20}$ aryl group, a $C_{6-20}$ fluoroaryl group, a $C_{1-20}$ heteroaryl group, a $C_{7-20}$ aralkyl group, a $C_{7-20}$ fluoroaralkyl group, a $C_{2-20}$ heteroaralkyl group, or a $C_{2-20}$ fluoroheteroaralkyl group, each of which is substituted or unsubstituted, wherein each $R^2$ is either separate or connected to the other group $R^2$ via a single bond or a linking group, and Ar is a substituted or unsubstituted $C_{6-30}$ aromatic organic group.

7. The photoresist composition of claim 1, wherein $M^+$ is an organic cation having Formula (VI):

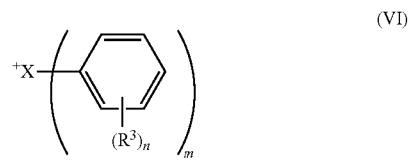

(VI)

wherein

X is I or S;

each $R^3$ is independently a halogen, a $C_{1-10}$ alkyl group, a $C_{1-10}$ fluoroalkyl group, a $C_{1-10}$ alkoxy group, a $C_{1-10}$ fluoroalkoxy group, a $C_{3-10}$ cycloalkyl group, a $C_{3-10}$ fluorocycloalkyl group, a $C_{3-10}$ cycloalkoxy group, a $C_{3-10}$ fluorocycloalkoxy group, or a $C_{6-10}$ alkoxycarbonylalkyleneoxy group;

each n is an integer of 0, 1, 2, 3, 4, and 5; and m is an integer of 2 or 3, provided that when X is I, m is 2, and where X is S, m is 3.

8. The photoresist composition of claim 1, wherein $M^+$ is an organic cation having Formulae (VII) or (VIII):

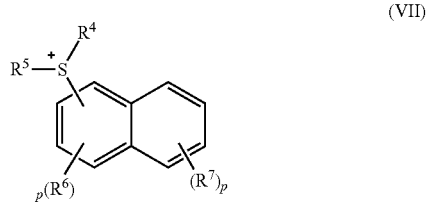

(VII)

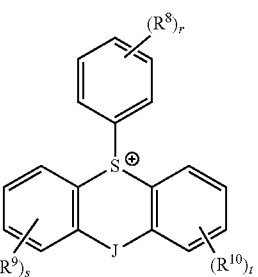

(VIII)

wherein $R^4$, $R^5$, $R^6$, $R^7$, $R^8$, $R^9$, and $R^{10}$ are each independently a halogen, —CN, —OH, a $C_{1-10}$ alkyl group, a $C_{1-10}$ fluoroalkyl group, a $C_{1-10}$ alkoxy group, a $C_{1-10}$ fluoroalkoxy group, a $C_{3-10}$ cycloalkyl group, a $C_{3-10}$ fluorocycloalkyl group, a $C_{3-10}$ cycloalkoxy group, or a $C_{3-10}$ fluorocycloalkoxy group, each of which except a halogen, —CN, and —OH is substituted or unsubstituted;

J is a single bond or a connecting group selected from S, O, and C=O, p is each independently an integer of 0, 1, 2, 3, or 4;

r is an integer of 0, 1, 2, 3, 4, and 5, and s and t are each independently an integer of 0, 1, 2, 3, and 4.

9. The photoresist composition of claim 1, wherein R comprises a polymerizable group, and wherein the photoacid generator is a polymerized unit of the acid-sensitive polymer.

10. A coated substrate, comprising: (a) a substrate having one or more layers to be patterned on a surface thereof; and (b) a layer of the photoresist composition of claim 1 over the one or more layers to be patterned.

11. A method of forming an electronic device, comprising: (a) applying a layer of the photoresist composition of claim 1 on a substrate; (b) patternwise exposing the photoresist composition layer to activating radiation; and (c) developing the exposed photoresist composition layer to provide a resist relief image.

12. A photoresist composition comprising:
an acid-sensitive polymer,
a solvent, and
a photoacid generator compound having Formulae (IIa) or (IIb):

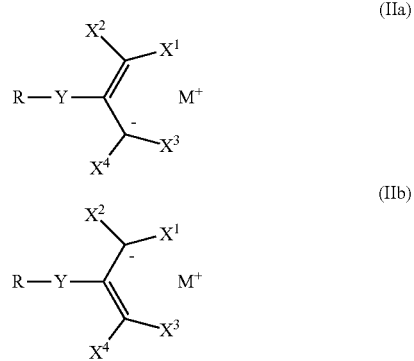

wherein:
$X^1$, $X^2$, $X^3$, and $X^4$ are each independently an electron-withdrawing group;
Y is a single bond or a linking group;
R is hydrogen, a straight chain or branched $C_{1-20}$ alkyl group, a straight chain or branched $C_{2-20}$ alkenyl group, a monocyclic or polycyclic $C_{3-20}$ cycloalkyl group, a monocyclic or polycyclic $C_{3-20}$ cycloalkenyl group, a monocyclic or polycyclic $C_{3-20}$ heterocycloalkyl group; a monocyclic or polycyclic $C_{3-20}$ heterocycloalkenyl group; a monocyclic or polycyclic $C_{3-20}$ aryl group, or a monocyclic or polycyclic $C_{1-20}$ heteroaryl group, each of which except hydrogen is substituted or unsubstituted; and
M is an organic cation.

13. The photoresist composition of claim 12, wherein the photoacid generator compound having Formula (II) does not contain a halogen atom.

14. The photoresist composition of claim 12, wherein the electron-withdrawing group does not contain fluorine.

15. A photoresist composition comprising:
an acid-sensitive polymer,
a solvent, and
a photoacid generator compound represented by:

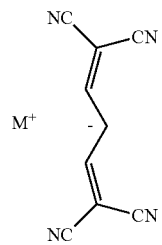

wherein M is an organic cation.

16. The photoresist composition of claim 1, wherein the photoacid generator compound having Formula (I) does not contain a halogen atom.

17. The photoresist composition of claim 1, wherein the electron-withdrawing group does not contain fluorine.

18. The photoresist composition of claim 2, wherein the photoacid generator compound having Formula (III) does not contain a halogen atom.

19. The photoresist composition of claim 2, wherein the electron-withdrawing group does not contain fluorine.

20. The photoresist composition of claim 5, wherein the photoacid generator compound having Formula (IV) does not contain a halogen atom.

21. The photoresist composition of claim 5, wherein the electron-withdrawing group does not contain fluorine.

* * * * *